(12) United States Patent
Solanki et al.

(10) Patent No.: US 11,051,693 B2
(45) Date of Patent: Jul. 6, 2021

(54) SYSTEMS AND METHODS FOR AUTOMATED END-TO-END EYE SCREENING, MONITORING AND DIAGNOSIS

(71) Applicant: EYENK, INC., Woodland Hills, CA (US)

(72) Inventors: Kaushal Mohanlal Solanki, Woodland Hills, CA (US); Christian Siagian, Woodland Hills, CA (US); Malavika Bhaskaranand, Woodland Hills, CA (US); Chaithanya Amai Ramachandra, Woodland Hills, CA (US); Sandeep Bhat Krupakar, Woodland Hills, CA (US); Nishit Umesh Parekh, Woodland Hills, CA (US)

(73) Assignee: EYENK, INC., Woodland Hills, CA (US)

( * ) Notice: Subject to any disclaimer, the term of this patent is extended or adjusted under 35 U.S.C. 154(b) by 230 days.

(21) Appl. No.: 16/234,301

(22) Filed: Dec. 27, 2018

(65) Prior Publication Data
US 2019/0200861 A1    Jul. 4, 2019

Related U.S. Application Data

(60) Provisional application No. 62/610,802, filed on Dec. 27, 2017.

(51) Int. Cl.
*A61B 3/14* (2006.01)
*G06F 3/01* (2006.01)
(Continued)

(52) U.S. Cl.
CPC .............. *A61B 3/14* (2013.01); *A61B 3/0075* (2013.01); *A61B 3/0083* (2013.01); *A61B 3/12* (2013.01);
(Continued)

(58) Field of Classification Search
CPC ........... A61B 3/14; A61B 3/12; A61B 3/0075; A61B 3/0083; G06N 3/08; G06N 20/00; G06N 3/02; G06N 3/006; G06F 3/013
See application file for complete search history.

(56) References Cited

U.S. PATENT DOCUMENTS 2,772,583 A * 12/1956 Harbaugh ........... F16H 61/0262
475/98
9,008,391 B1    4/2015 Solanki et al.
(Continued)

OTHER PUBLICATIONS

Boukamcha, H., et al., "Automatic landmark detection and 3D Face data extraction", Journal of Computational Science, 2017, vol. 21, pp. 340-348.
(Continued)

*Primary Examiner* — Cara E Rakowski
(74) *Attorney, Agent, or Firm* — One LLP; Joseph K. Liu

(57) ABSTRACT

System and method for fully automated end-to-end eye screening with automated medical acquisition and analysis. The system includes an eye imaging device, a mechanism that moves the imaging device, a computing platform that guides the movement mechanism, a user interface, and an electronic display device and/or printer to provide the screening, monitoring, and/or diagnosis report.

19 Claims, 11 Drawing Sheets

(51) Int. Cl.
G06N 3/08 (2006.01)
A61B 3/12 (2006.01)
A61B 3/00 (2006.01)
G06N 20/00 (2019.01)

(52) U.S. Cl.
CPC .............. *G06F 3/013* (2013.01); *G06N 3/08* (2013.01); *G06N 20/00* (2019.01)

(56) References Cited

U.S. PATENT DOCUMENTS

| | | | | |
|---|---|---|---|---|
| 2005/0068496 | A1* | 3/2005 | Ichikawa | A61B 3/14 351/206 |
| 2009/0195750 | A1* | 8/2009 | Isogai | A61B 3/152 351/208 |
| 2014/0028977 | A1* | 1/2014 | Umekawa | A61B 3/152 351/208 |
| 2020/0069175 | A1* | 3/2020 | Kumagai | A61B 3/102 |

OTHER PUBLICATIONS

Comaniciu, D., et al., "Kernel-based Object Tracking", IEEE Transactions on Pattern Analysis and Machine Intelligence, 2003, vol. 25, No. 5, pp. 564-577.

Dias, J. M. P., et al., "Evaluation of retinal image gradability by image features classification", Procedia Technology, 2012, vol. 5, pp. 865-875.

Giancardo, L., et al., "Quality Assessment of Retinal Fundus Images using Elliptical Local Vessel Density", New Developments in Biomedical Engineering, 2010, pp. 201-224.

International Diabetes Federation: IDF Diabetes Atlas, 7th ed., 2015, pp. 1-140.

Kalal, Z., et al., "Tracking-Learning-Detection", IEEE Transactions on Pattern Analysis and Machine Intelligence, 2010, vol. 6, No. 1, pp. 1-14.

Katuwal, G. J., et al., "Automatic Fundus Image Field Detection and Quality Assessment", 2013 Western New York Image Processing Workshop, Rochester, NY, pp. 9-13.

King, D. E., "Dlib-ml" A Machine Learning Toolkit, Journal of Machine Learning Research, 2009, vol. 10, pp. 1755-1758.

Lai, H., et al., "Deep Recurrent Regression for Facial Landmark Detection", IEEE Transactions on Circuits and Systems for Video Technology, 2016, vol. 28, No. 5, pp. 1-13.

Li, H., et al., "DeepTrack: Learning Discriminative Feature Representations Online for Robust Visual Tracking", IEEE Transactions on Image Processing, 2016, vol. 25, No. 4, pp. 1834-1848.

Mahapatra, D., et al., "Retinal Image Quality Classification Using Saliency Maps and CNNs", Machine Learning in Medical Imaging, 2016, pp. 172-179.

Mnih, V., et al., "Human-level control through deep reinforcement learning", Nature. 2015, vol. 518, pp. 529-533.

Nam, H., et al., "Learning Multi-Domain Convolutional Neural Networks for Visual Tracking", 2016 Proceedings of IEEE Conference on Computer Vision and Pattern Recognition, Las Vegas, NV, pp. 4293-4302.

Paulus, J., et al., "Automated Quality Assessment of Retinal Fundus Photos", International Journal of Computer Assisted Radiology and Surgery, 2010, vol. 5, pp. 557-564.

Perakis, P., et al., "3D Facial Landmark Detection under Large Yaw and Expression Variations", IEEE Transactions on Pattern Analysis and Machine Intelligence, 2013, vol. 35, No. 7, pp. 1552-1564.

Saha, S. K., et al., "Deep Learning for Automated Quality Assessment of Color Fundus Images in Diabetic Retinopathy Screening", Journal of Digital Imaging, 2017, vol. 31, No. 10, pp. 1-23.

Saragih, J. M., et al., "Deformable Model Fitting by Regularized Landmark Mean-Shift", Int J Comput Vis, 2011, vol. 91, pp. 200-215.

Shi, J., et al., "Good Features to Track", 1994 Proceedings of IEEE Conference on Computer Vision and Pattern Recognition, Seattle, WA, pp. 593-600.

Sun, Y., et al., "Deep Convolutional Network Cascade for Facial Point Detection", Proceedings of the 2013 IEEE Conference on Computer Vision and Pattern Recognition, Washington, D.C., pp. 3476-3483.

Wang, N., et al, "Learning a Deep Compact Image Representation for Visual Tracking", Proceedings of the 26$^{th}$ International Conference on Neural Information Processing Systems, 2013, vol. 1, pp. 809-817.

Xiong, X., et al., "Supervised Descent Method and Its Applications to Face Alignment", Proceedings of the 2013 IEEE Conference on Computer Vision and Pattern Recognition, Washington, D.C., pp. 532-539.

Zhang, J., et al., "Coarse-to-Fine Auto-Encoder Networks (CFAN) for Real-Time Face Alignment", Computer Vision—ECCV 2014, Lecture Notes in Computer Science, pp. 1-16.

Zhang, K., et al., "Robust Visual Tracking via Convolutional Networks", IEEE Transactions on Image Processing, 2016, vol. 25, No. 4, pp. 1779-1792.

Zhang, Z., et al., "Learning Deep Representation for Face Alignment with Auxiliary Attributes", IEEE Transactions on Pattern Analysis and Machine Intelligence, 2016, pp. 1-14.

Zhou, H., et al., "Object tracking using SIFT features and mean shift", Computer Vision and Image Understanding, 2009, vol. 113, pp. 345-352.

Zhu, S., et al., "Face Alignment by Coarse-to-Fine Shape Searching", 2015 IEEE Conference on Computer Vision and Pattern Recognition, Boston, Massachusetts, pp. 4998-5006.

Zhu, X., et al., "Face Detection, Pose Estimation, and Landmark Localization in the Wild", 2012 IEEE Conference on Computer Vision and Pattern Recognition, Providence, Rhode Island, pp. 1-8.

* cited by examiner

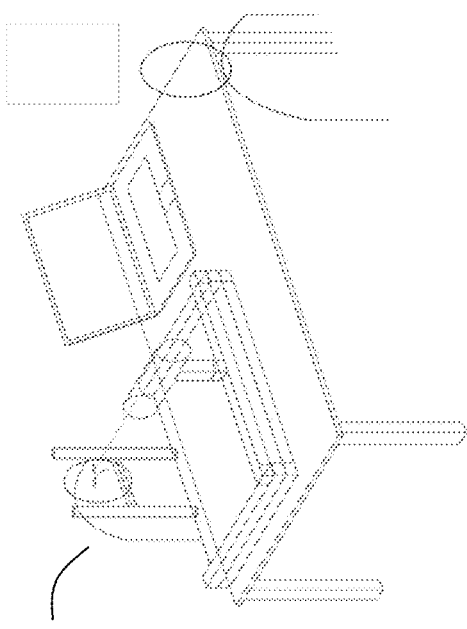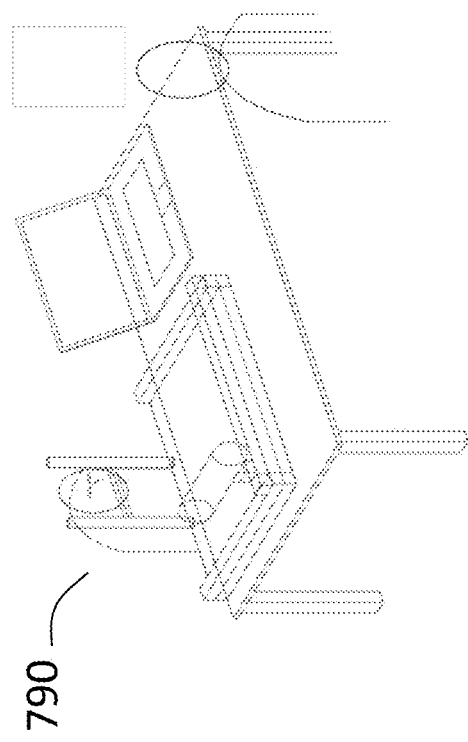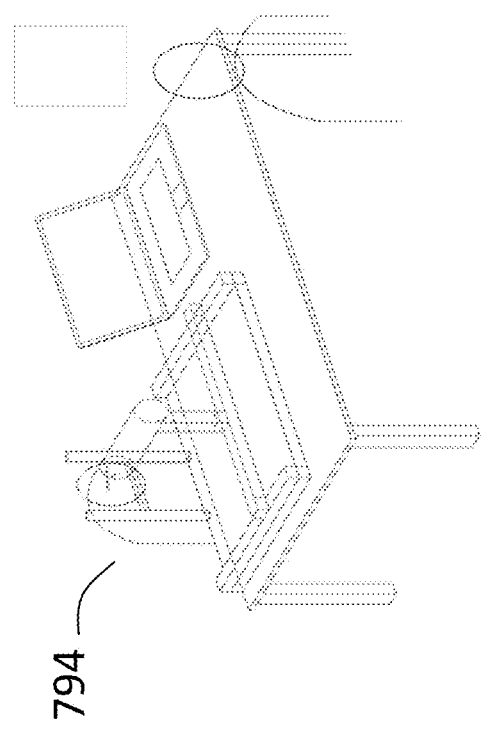
FIG. 7C

SYSTEMS AND METHODS FOR AUTOMATED END-TO-END EYE SCREENING, MONITORING AND DIAGNOSIS

PRIORITY INFORMATION

This application claims the benefit of priority under 35 U.S.C. § 119(e) to U.S. Provisional Application No. 62/610,802, filed Dec. 27, 2017, entitled "SYSTEMS AND METHODS FOR AUTOMATED END-TO-END EYE SCREENING, MONITORING AND DIAGNOSIS".

TECHNICAL FIELD

The subject matter described herein relates generally to fully automated end-to-end screening, monitoring and diagnosis of systemic and/or retinal diseases and disorders with automated medical acquisition and analysis. More particularly, it relates to the use of robotic/mechatronic systems/methods for automated image acquisition where the imaging device is moved to image the required anatomical structures and image analysis systems/methods for automated generation of screening, monitoring, and diagnosis outcomes.

BACKGROUND

Retinal fundus photography (often referred to as fundus photography and including color fundus photography, scanning laser ophthalmoscopy based ultra-widefield photography, and optical coherence tomography modalities) is frequently used as a screening, monitoring, or diagnostic tool for multiple eye diseases, such as diabetic retinopathy, glaucoma, and age-related macular degeneration. Screening, monitoring, and diagnosis using fundus photographs allows for patients without access to eye-care specialists to be screened for multiple diseases. Fundus photography and any subsequent analysis can only be effective with the consistent capture of good quality photographs which in many cases requires a highly trained and experienced technician.

A set of fundus photographs belonging to a particular patient is considered to be of good/gradable quality when the fundus photographs:
- capture the regions of the retina that are required for the screening/monitoring/diagnosis of a given disease
- have sufficient illumination and clarity to allow for the examination of the anatomical and pathological features of interest; and
- are free of artifacts including but not limited to, eyelashes, dust, and smudges on the lens.

However, the number of technicians trained for fundus photography is orders of magnitude smaller than that needed to screen the large and growing population that require screening (e.g. 415 million diabetic patients worldwide need annual diabetic retinopathy screening. See, INTERNATIONAL DIABETES FEDERATION: *IDF Diabetes Atlas, 7th edn*. Brussels, Belgium: International Diabetes Federation, 2015 [INTE15]). This gap in the number of trained technicians can only be met by a system that fully automates the capture and analysis of fundus photographs for screening, thus eliminates the need for a trained technician-in-the-loop. Such systems can potentially make eye screening more efficient, cost-effective, reproducible, and accessible.

A need therefore exists to develop a device and method that provide ease of use, accuracy, speed, portability and affordability, and that overcome these and other limitations of the prior art.

SUMMARY

This summary and the following detailed description should be interpreted as complementary parts of an integrated disclosure, which parts may include redundant subject matter and/or supplemental subject matter. An omission in either section does not indicate priority or relative importance of any element described in the integrated application. Differences between the sections may include supplemental disclosures of alternative embodiments, additional details, or alternative descriptions of identical embodiments using different terminology, as should be apparent from the respective disclosures.

System and method for fully automated end-to-end screening with automated medical acquisition and analysis are provided in the present disclosure. Generally, the present disclosure includes system and method that relate to automated capture of gradable/screenable fundus photographs or video sequences using eye imaging devices attached to a robotic moving platform; automated analysis of the captured photographs or videos to screen for, monitor, and diagnose particular diseases; and providing of a screening, monitoring, and diagnosis outcome. The present disclosure may screen a patient for multiple diseases with easy-to-use user interfaces, including but not limited to, the push of a button/switch, touch-activated electronic display (touchscreen) interface inputs, pressure sensors/activators in head rest, and/or voice-activated controls. In some embodiments, the eye imaging device may be an existing off-the-shelf and portable camera unit. In some embodiments, the robotic moving platform may be a level surface or an arm.

In some aspects, the system and method meet or exceed the following requirements:

Ease of use: The system and method are easy to operate, for example, using an intuitive user interface. This reduces the training time and educational background necessary for the operators/users.

Accuracy: The system and method may have a 90% or higher rate of success in acquiring gradable photographs in a fully-automated mode. In some embodiments, the system and method may allow for a semi-automatic or fully-manual mode for override by the operator/user. One example is when certain gradable photographs are desired.

Speed: The system and method may capture photographs of both eyes of a patient in a short amount of time, for example, under 2 minutes. This helps improve patient experience and comfort.

Portability and affordability: The system and method may be compact, portable, and relatively inexpensive to enable large scale deployment in a variety of clinic conditions.

In some embodiments of such a system, a patient sits on a chair in front of a robotic system to which a portable imaging device is attached. When the operator, possibly untrained or minimally trained, activates the screening procedure using the user interfaces, the robotic moving platform moves the imaging device in a manner to obtain gradable photographs or video sequences of the eye and/or some of its anatomical structures. The system then analyzes these photographs or video sequences to screen for multiple diseases and presents a screening and diagnosis report/outcome, for example to the patient.

In some embodiments, the system is self-operated. Here, the untrained operator may be the patient being screened.

In some embodiments, the system captures the photographs using a hand-held imaging device by a trained photographer instead of the robotic system. The hand-held imaging device may be coupled with an electronic display to aid the operator in correctly aligning the imaging device.

In some embodiments, the fully automated system may have the following major components: an eye imaging device, a moving platform capable of moving the imaging device in 3-dimensional space, a computing device that enables the automated analysis, a user interface, and an optional electronic display device and/or printer to provide the screening, monitoring, and/or diagnosis report, for example to the patient.

In addition to, in alternative of having the fully automatic acquisition and analysis of photographs, certain embodiments of the device may also allow for a semi-automatic or fully manual override for photograph or video sequence acquisition by the operator/user, for example, when certain gradable photographs cannot be obtained in a fully automated mode. In the semi-automatic mode, the operator may perform simple tasks such as centering the imaging device's view on the target eye. In the fully manual mode, a set of manual controls is provided, where the technician can steer the imaging device to center on the eye and move to the proper working distance to capture a gradable photograph.

The system may also include system safety precautions including but not limited to, a hard mechanical limit on the moving platform's range of motion and a programmed limit on the moving platform's range of motion. These safety precautions prevent the system from injuring the patient or the operator, and/or harming the device itself.

Other systems, devices, methods, features and advantages of the subject matter described herein will be or will become apparent to one with skill in the art upon examination of the following figures and detailed description. It is intended that all such additional systems, devices, methods, features and advantages be included within this description, be within the scope of the subject matter described herein, and be protected by the accompanying claims. In no way should the features of the example embodiments be construed as limiting the appended claims, absent express recitation of those features in the claims.

BRIEF DESCRIPTION OF THE FIGURES

The details of the subject matter set forth herein, both as to its structure and operation, may be apparent by study of the accompanying figures, in which like reference numerals refer to like parts. The components in the figures are not necessarily to scale, emphasis instead being placed upon illustrating the principles of the subject matter. Moreover, all illustrations are intended to convey concepts, where relative sizes, shapes and other detailed attributes may be illustrated schematically rather than literally or precisely.

FIG. 7C illustrates exemplary positions of the imaging device at various phases of the image acquisition process, in accordance with an embodiment of the present disclosure.

DETAILED DESCRIPTION

Before the present subject matter is described in detail, it is to be understood that this disclosure is not limited to the particular embodiments described, as such may, of course, vary. It is also to be understood that the terminology used herein is for the purpose of describing particular embodiments only, and is not intended to be limiting, since the scope of the present disclosure will be limited only by the appended claims.

Figure 3:
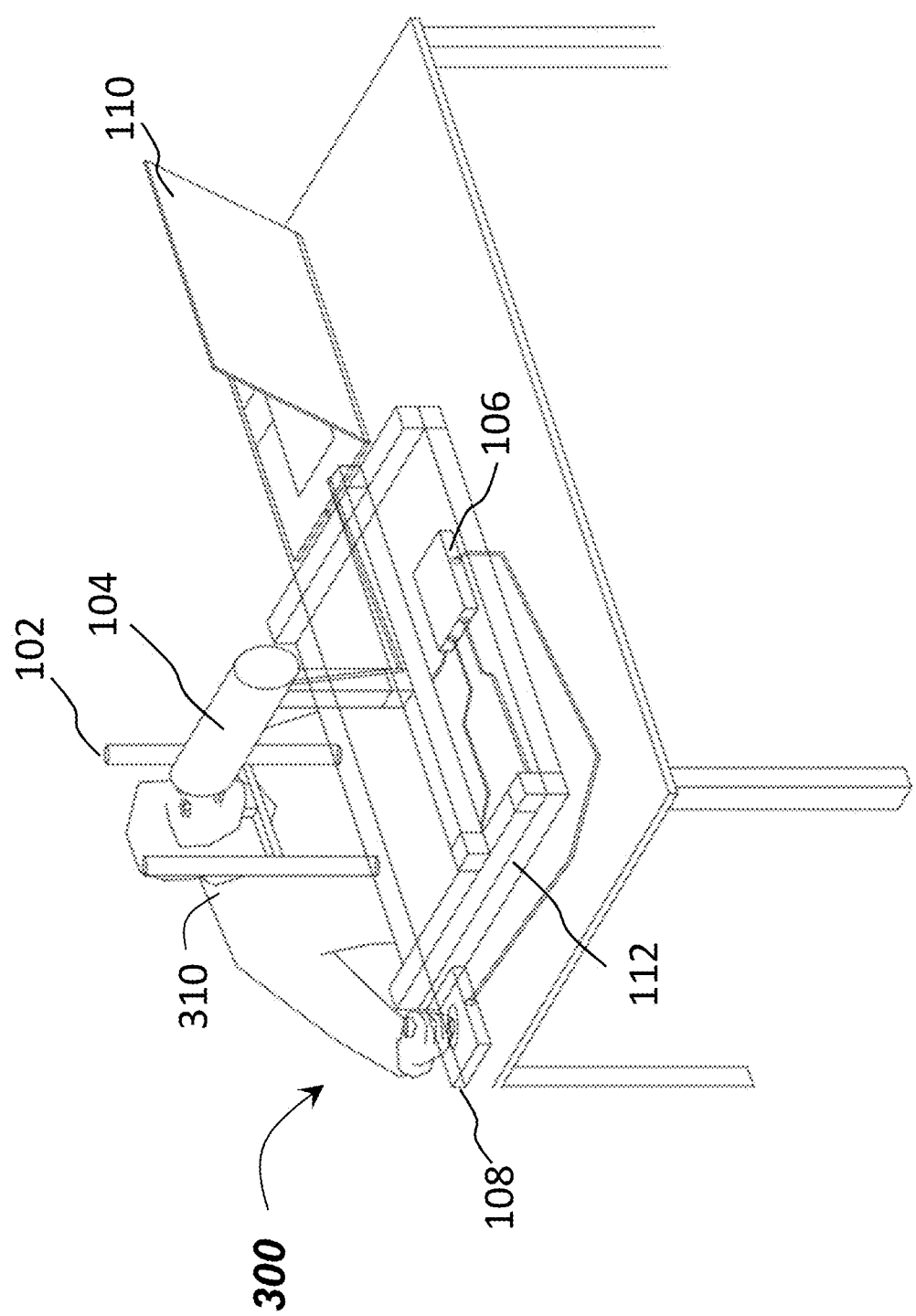
FIG. 3 illustrates an exemplary self-operated end-to-end eye screening with automated medical acquisition and analysis system, in accordance with an embodiment of the present disclosure.
Figure 4:
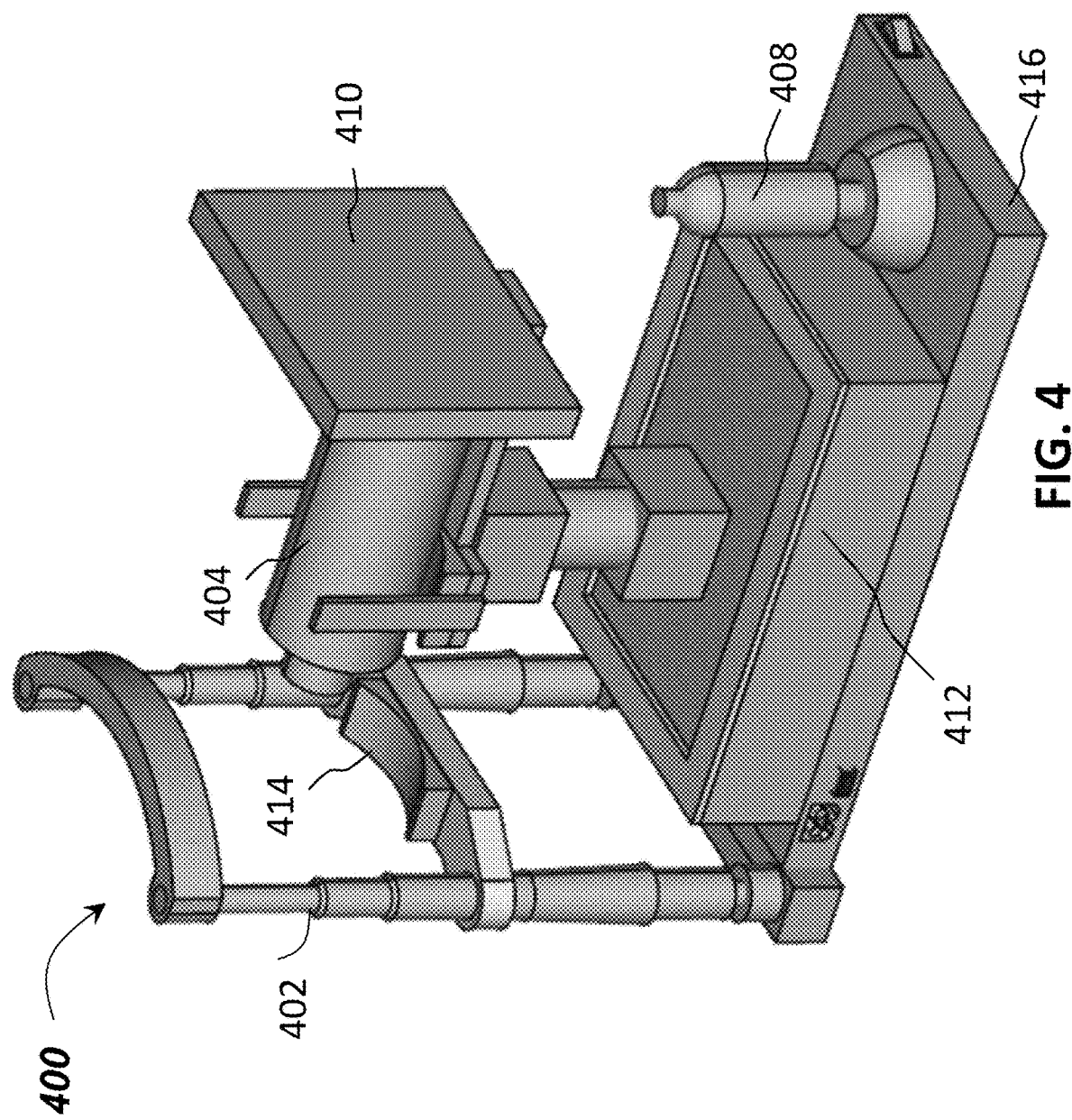
FIG. 4 illustrates another exemplary end-to-end eye screening with automated medical acquisition and analysis, in accordance with an embodiment of the present disclosure.
Figure 5:
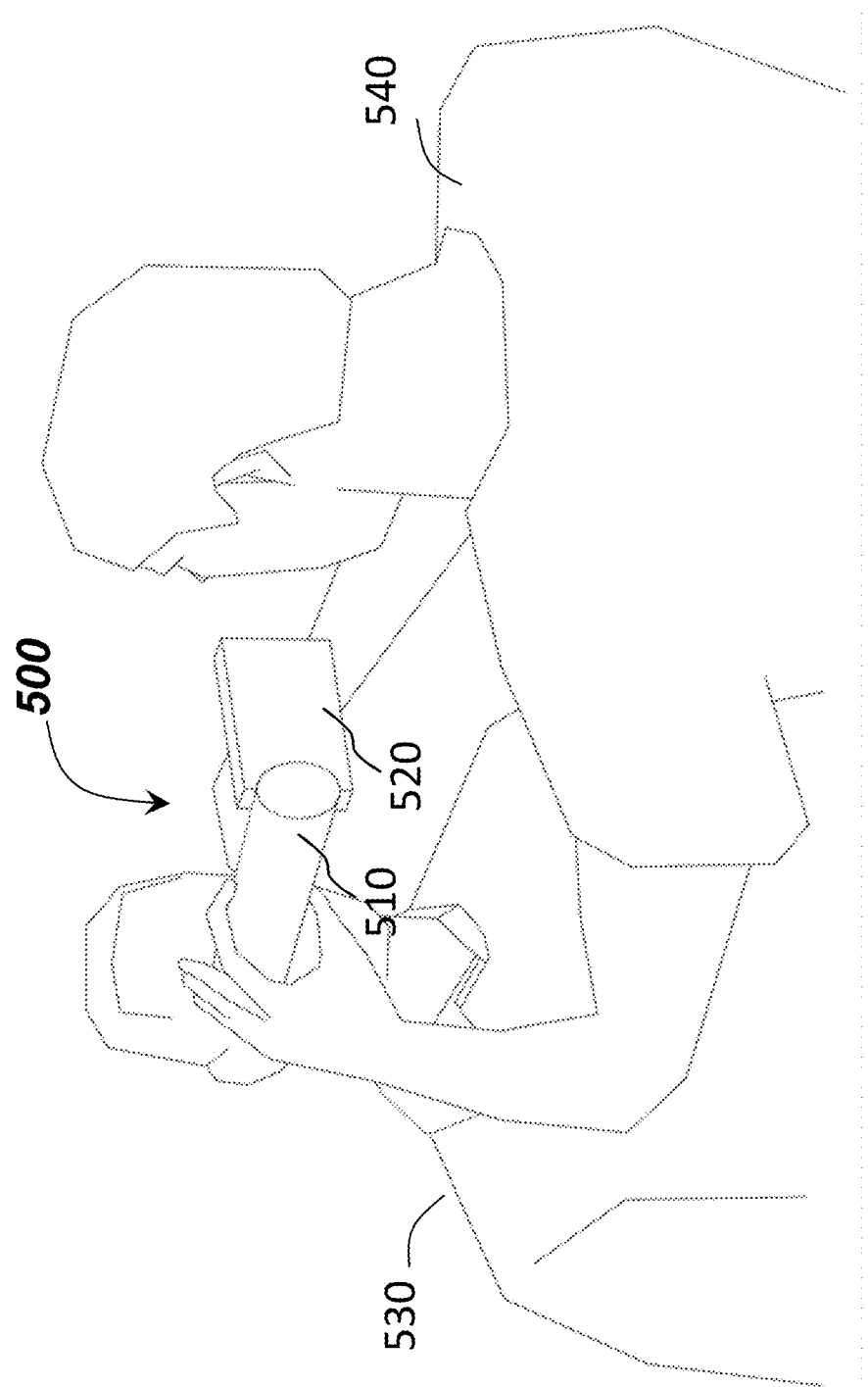
FIG. 5 illustrates an exemplary hand-held system for end-to-end eye screening with automated medical acquisition and analysis, with a hand-held imaging device and a coupled electronic display in accordance with an embodiment of the present disclosure.

FIGS. 1-9 illustrate embodiments of systems and methods for fully automated end-to-end eye screening with automated medical acquisition and analysis. Generally, the hardware components of the disclosure may comprise an eye imaging device (which, in some embodiments, may be an off-the-shelf camera), a mechanism that moves the imaging device, the computing platform that guides the movement mechanism, a user interface, and an electronic display device and/or printer to provide the screening, monitoring, and/or diagnosis report, for example to the patient. In some embodiments, the hardware components may be modified or implemented in multiple forms. In some embodiments, the present disclosure includes four main processing/control software procedures or modules (illustrated in FIG. 6): a user interface module to interact with an operator; retinal image acquisition module to control the hardware and capture one or more images (or photographs) or video sequences; the analysis module to process the images/videos to screen for, monitor, or diagnose diseases; and a module to store, report, and perform necessary tasks given the outcome. A video sequence can be considered as a series of multiple images and therefore, henceforth in this disclosure, the use of image and images also include video and video sequences. The feedback loop 610 illustrated as a dashed arrow in FIG. 6 can be optionally added to allow the system to recapture images or capture additional images based on whether the current images or portions of current images provide sufficient data/evidence for the automated analysis to generate a screening/diagnosis outcome. In some embodiments, these modules can be presented in many forms, some may be coupled, omitted, or implemented in forms that are not entirely software. For example, in the hand-held form (as illustrated in FIG. 5), the system takes advantage of the technician's skills in positioning the hand-held imaging device and the automated system evaluates whether the current image is of sufficient quality for automated analysis, and if not prompt the technician to retake the image. It should be noted that a technician may also be referred to herein as an operator or user.

Figure 2:
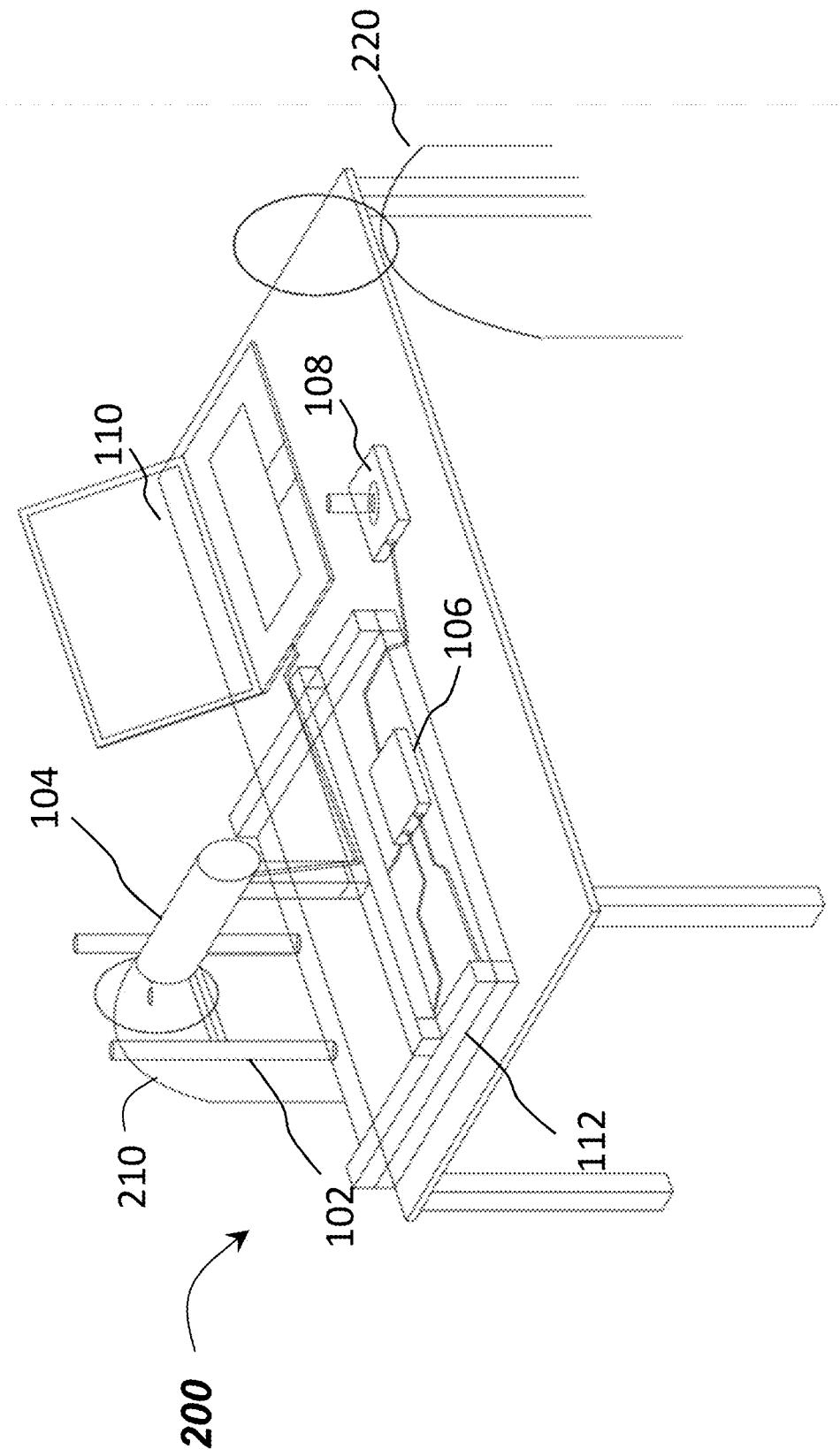
FIG. 2 illustrates an exemplary end-to-end eye screening with automated medical acquisition and analysis system where the imaging device is operated by a technician, in accordance with an embodiment of the present disclosure.

FIG. 2 illustrates an exemplary embodiment of the system of the present disclosure where the patient 210 sitting on a chair in front of a robotic system 200 to which an imaging device 104 is attached. When the operator 220, possibly untrained or minimally trained, activates the method of the present disclosure using one of the input methods, the moving platform 112 moves the imaging device 104 in a manner to obtain gradable photographs. These photographs are then analyzed to screen for multiple eye diseases and a screening report/outcome is presented to the patient. In an aspect, the photographs are fundus photographs.

In another exemplary embodiment of this system, illustrated in FIG. 3, the system 300 may be self-operated. Here, the untrained operator may be the patient 310 being screened.

In FIG. 5, in another exemplary embodiment of the system, the photographs are captured using a hand-held imaging device 500 by a trained photographer 540 instead of the robotic system.

Figure 6:
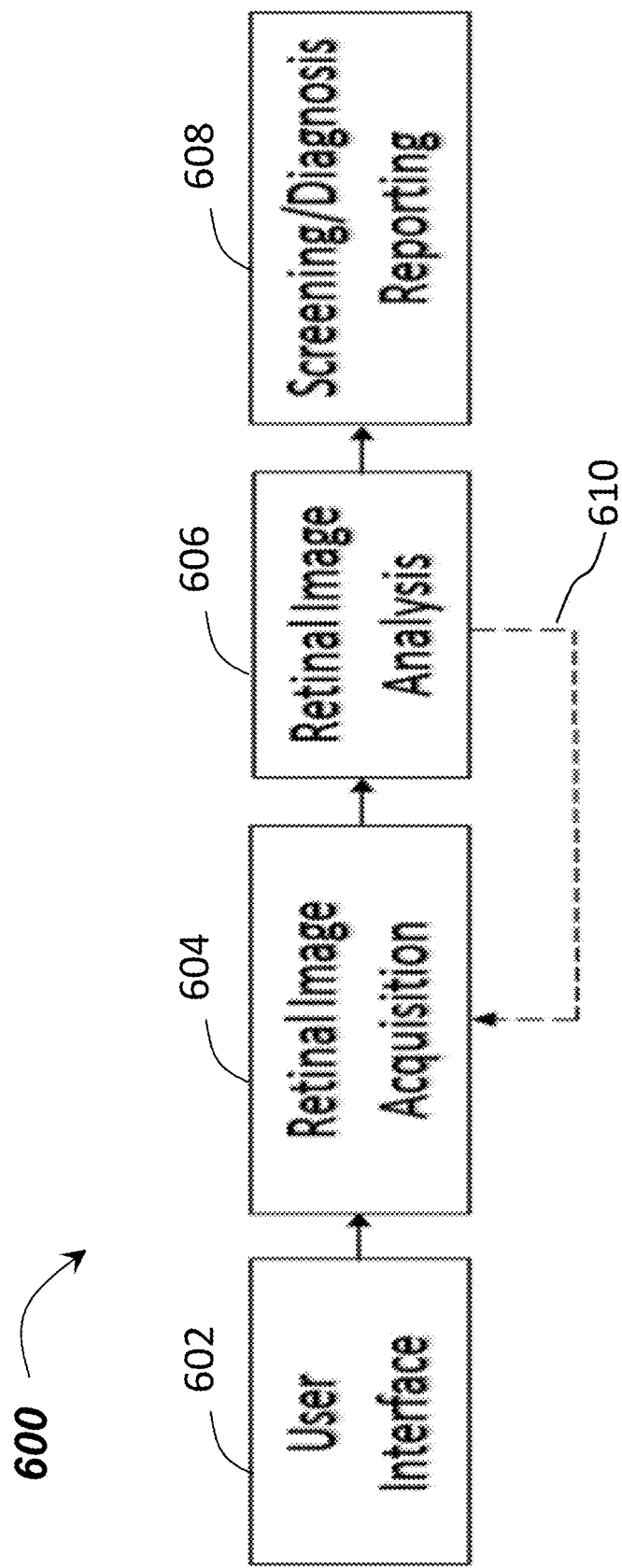
FIG. 6 illustrates exemplary high-level diagram of components of an end-to-end eye screening with automated medical acquisition and analysis, in accordance with an embodiment of the present disclosure.

FIG. 6 illustrates high-level exemplary processing/control components of the system of the disclosure.

Hardware/Mechanical Components

Figure 1:
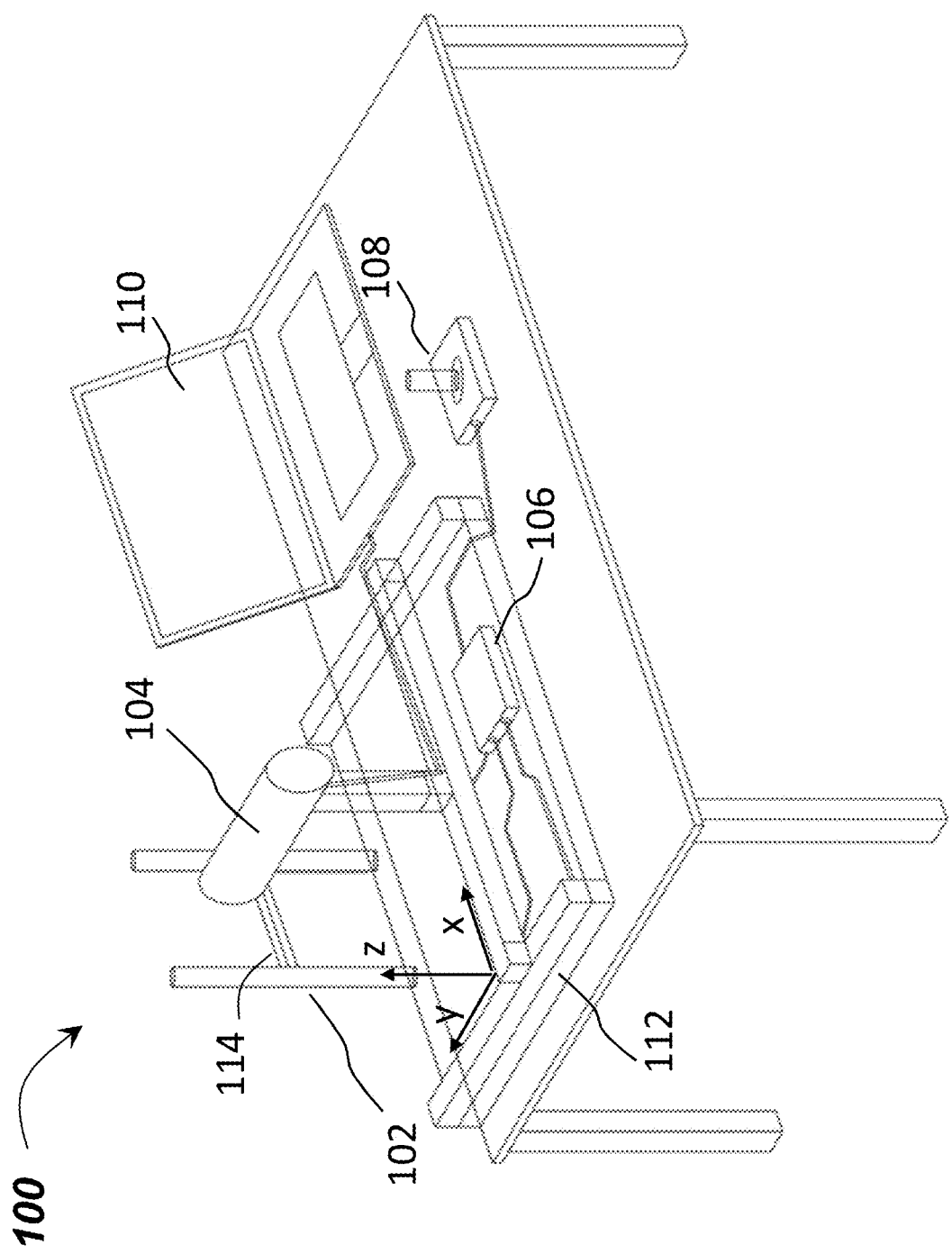
FIG. 1 illustrates an exemplary end-to-end eye screening with automated medical acquisition and analysis, in accordance with an embodiment of the present disclosure.

FIG. 1 illustrates an exemplary embodiment of the mechanical components of the fully automated robotic version of the system 100 of the present disclosure. The main part is a moving platform 112 on which is mounted the imaging device 104. Both the moving platform 112 and the imaging device 104 are connected to the computing platform or computer 110. In this embodiment the imaging device 104 may be a portable fundus camera.

The moving platform 112 may be coupled to a controller 106 that is connected to the computer 110 as well as three sets of motors, each responsible for motion of the imaging device 104 along one of the spatial x-, y-, and z-axes. The connections allow the controller to relay motion, inducing commands to the motors from the processing/control system. The controller may filter these commands so that the hardware only executes commands either in desired safety limits (for example, when an axis is about to hit a hardware limit), or in accordance to the current dynamics of the system (for example, if the system wants to reverse the motor's direction while it is currently moving at a high speed, the next command should be one that first reduces the velocity to a smooth stop, before proceeding to move in reverse).

To aid the acquisition process and enhance system safety, the moving platform 112 may also be equipped with other sensors to guide its motion, including but not limited to additional cameras, proximity sensors (e.g. infrared or laser), or attitude proprioceptive sensor (e.g. accelerometer, gyroscope). These sensors may be mounted on the platform, on the imaging device, separately by itself, or in other places, combinations, or configurations. A head rest 102, which may comprise of parts intended for the patient to rest his/her forehead, chin, and/or cheekbones, may be included in the system to hold the patient's head steady for the duration of the image acquisition (photography) process. Furthermore, there may be other accessories that can be added, including but not limited to, a fixation target to direct the patient's gaze.

The system may include a set of manual controls, for example, joystick 108, to allow the operator to manually override the operation, if needed.

In some embodiments, the system may include a touch-activated electronic display, or voice commands to assist the movement of the imaging device.

FIG. 4 illustrates another exemplary embodiment of the mechanical components of the fully automated robotic version of the system 400 of the present disclosure. System 400 may include moving platform 412 on which is mounted the imaging device 404. Both the moving platform 412 and the imaging device 404 are connected to the computing platform or computer 416. An electronic display 410 is connected to the imaging device 404 and the computing platform 416. In this embodiment the imaging device 404 may be a portable fundus camera.

The moving platform 412 may be coupled to a controller (not shown) that is connected to the computer 416 as well as three sets of motors, each responsible for motion of the imaging device 104 along one of the spatial x-, y-, and z-axes. The connections allow the controller to relay motion, inducing commands to the motors from the processing/control system. The controller may filter these commands so that the hardware only executes commands either in desired safety limits (for example, when an axis is about to hit a hardware limit), or in accordance to the current dynamics of the system (for example, if the system wants to reverse the motor's direction while it is currently moving at a high speed, the next command should be one that first reduces the velocity to a smooth stop, before proceeding to move in reverse).

To aid the acquisition process and enhance system safety, the moving platform 412 may also be equipped with other sensors to guide its motion, including but not limited to additional cameras, proximity sensors (e.g. infrared or laser), or attitude proprioceptive sensor (e.g. accelerometer, gyroscope). These sensors may be mounted on the platform, on the imaging device, separately by itself, or in other places, combinations, or configurations. A head rest 402, which may comprise of parts intended for the patient to rest his/her forehead, chin, and/or cheekbones, may be included in the system to hold the patient's head steady for the duration of the image acquisition (photography) process. Furthermore, there may be other accessories that can be added, including but not limited to, a fixation target to direct the patient's gaze.

The system may also include a set of manual controls, for example, joystick 408, to allow the operator to manually override the operation, if needed.

Processing/Control Components

An exemplary processing/control system 600 of the present disclosure (illustrated in FIG. 6) may comprise four sub-systems. A user interface sub-system 602 enables the operator to start the process and/or calibrate the system. The image acquisition sub-system 604 enables the control of the moving platform and the imaging device to capture the required photographs. The image analysis sub-system 606 analyzes the photographs/images captured to automatically provide one or more screening/monitoring/diagnostic outcomes. The feedback loop illustrated as a dashed arrow 610 in FIG. 6 can be performed to allow the system to recapture images or capture additional images based on whether the current images or portions of current images provide sufficient evidence for the automated analysis to generate a screening/monitoring/diagnostic report at 608. Methods for performing image analysis are similar to the methods described in "Systems and Methods for Processing Retinal Images for Screening of Diseases or Abnormalities" (Solanki, Kaushal Mohanlal; Bhat Krupakar, Sandeep; Amai Ramachandra, Chaithanya; and Bhaskaranand, Malavika) [SBAB15]. The screening/diagnosis report sub-system 608 may generate a report with the outcomes generated by the image analysis sub-system 606 to an electronic display device and/or printer and can be initiated by the user interface.

Figure 7A:
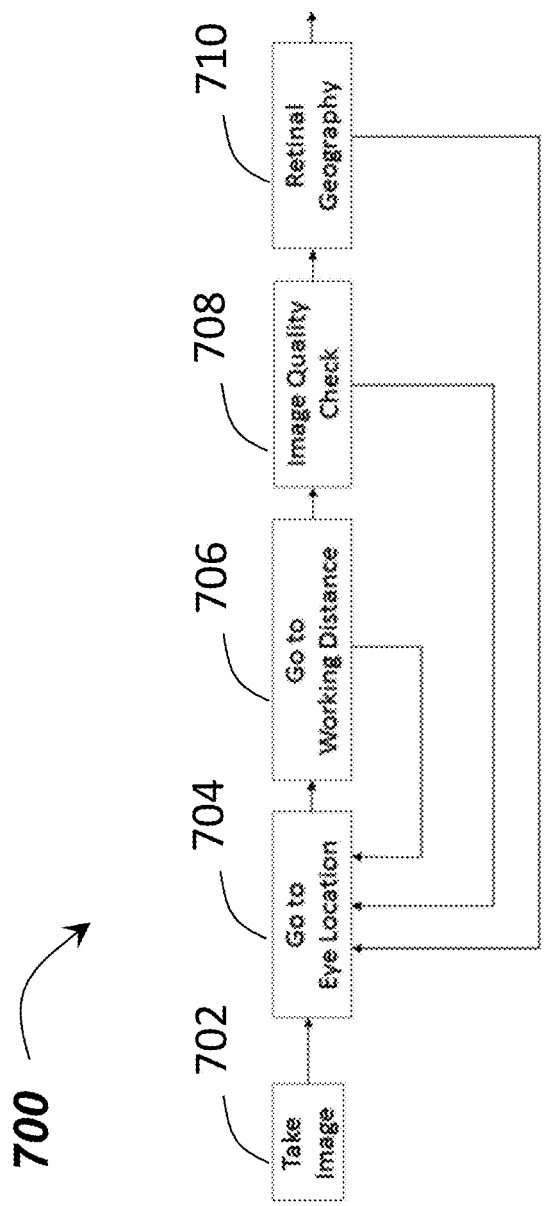
FIGS. 7A and 7B illustrate exemplary process flow diagrams of an end-to-end eye screening with automated medical acquisition and analysis, in accordance with an embodiment of the present disclosure.
Figure 7B:
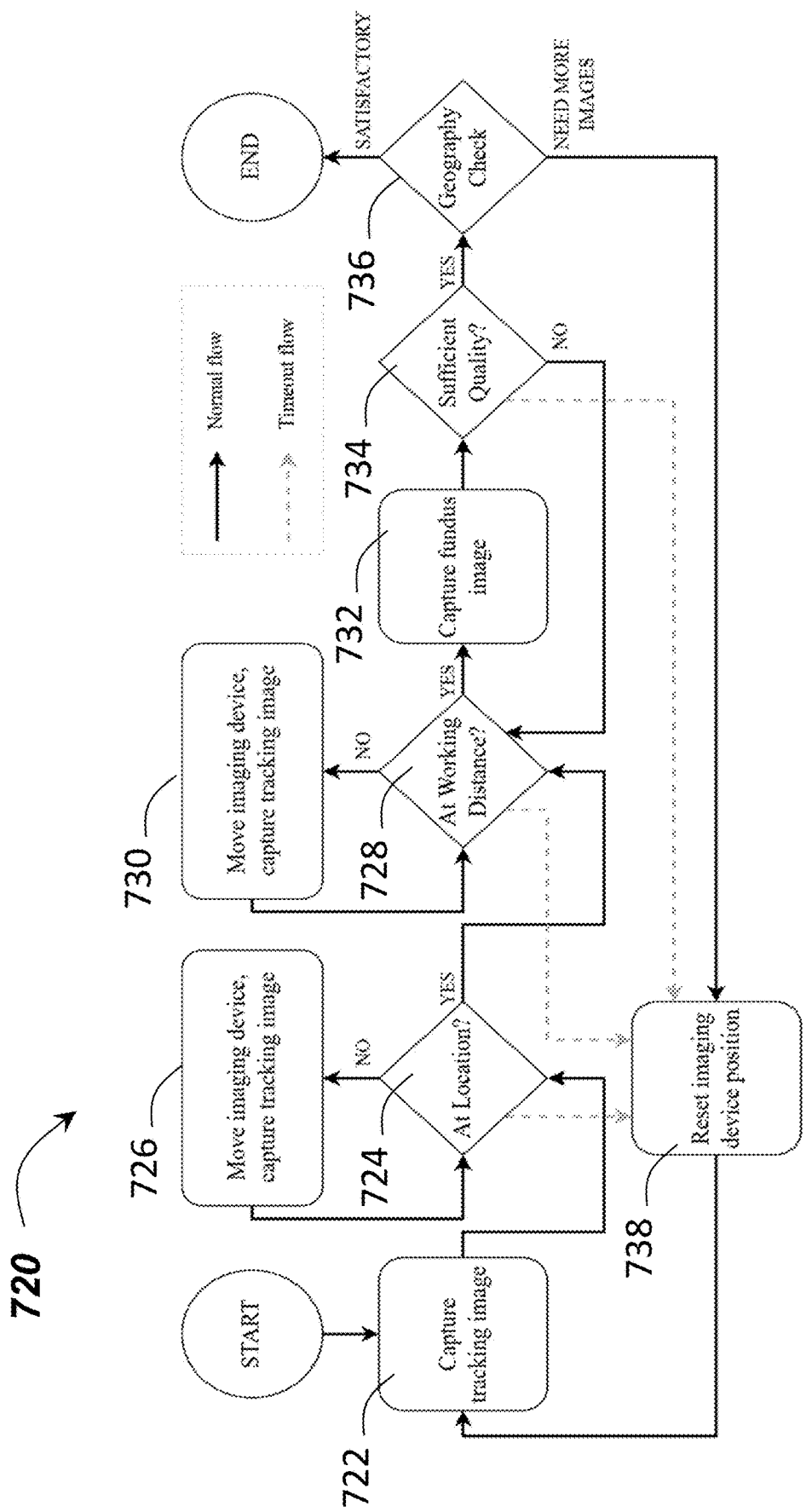

FIGS. 7A and 7B provide further details of the processing/control sub-systems. FIG. 7A illustrates a high-level diagram 700 of an image acquisition sub-system. An exemplary image acquisition sub-system 720 is illustrated with more details in FIG. 7B. In some aspects, it is responsible for moving the imaging device to capture high quality images. The system accommodates a broad range of intrinsic and extrinsic confounding conditions, including but not limited to the patient and eye movement during the process; varying appearances of faces, eyes, pupil (particularly pupil diameter), and retina (if retinal images are to be captured); and various environmental lighting or room conditions. Additionally, in order to maintain the patient's comfort, the procedure duration may be as short as necessary. Furthermore, mechanisms that can lead to patient discomfort, including but not limited to, extended duration of a bright light pointed towards the eye, may be minimized. This image acquisition sub-system relies on inputs from the imaging device and, in some embodiments, from other sensors including but not limited to additional cameras, proximity sensors (e.g. infrared or laser), or attitude proprioceptive sensor (e.g. accelerometer, gyroscope).

As shown in FIGS. 7A and 7B, the image acquisition sub-system performs a number of tasks: move the imaging device to a location specified by the desired eye (at 704, 724, 726), place the imaging device at a working distance away from said eye (at 706, 728, 730), perform image quality check (at 708, 734), and in some embodiments, for example where the imaging device is a retinal camera, perform retinal geography check (at 710, 736). During the procedure, the images may be continuously input into the sub-system at a constant rate and are processed, regardless of the current task.

In some embodiments, at the start of the process (prior to image acquisition), since the imaging device can be at a random location, as shown by 790 in FIG. 7C, the system must perform the first task to move the imaging device in the X, Y and Z directions to roughly direct it at the target eye, as shown by 792 in FIG. 7C. During this procedure, the imaging device may be maintained at a minimum distance from the target eye to allow for locating the eye by imaging a sufficient portion of the face (as shown for example, 902 in FIG. 9). The techniques to solve this task are described in the CENTERING THE EYE section below. This task may be repeated at any time if the patient changes body or head position, saccades, or blinks, as such, the system needs to re-center the imaging device such that the target eye is in its field of view.

The system may also re-center the eye in the imaging device's field of view if any of the sub-modules following it repeatedly fails for a pre-specified amount of time, as dep.

The second task (at 706, 728, 730) is to move the imaging device toward the eye while maintaining the pupil in the center of the imaging device's field of view. At the end of this phase, the imaging device is at a working distance away from the eye, and in certain embodiments where the imaging device is a fundus camera, portions of the retina are in the field of view (as shown, for example, 904 in FIG. 9). The techniques to solve this task are described in the MOVING TO WORKING DISTANCE section.

For the hand-held embodiment of the system, it may be assumed that when the system is not being moved by the technician (detected using attitude proprioceptive sensors), it is positioned close to the correct working distance.

The image acquisition sub-system then performs an image quality check (at 708, 734) using techniques described in the IMAGE QUALITY ASSESSMENT section. To increase the robustness of the implementation, one embodiment of the system may capture a number of images while close to the working distance, evaluate the quality of all such images, and subsequently select one or more images with highest quality for further analysis.

In certain embodiments where the imaging device is a fundus camera, once an image passes the image quality check, a specific embodiment of the system then checks the retinal geography covered by the image (at 710, 736). If the image analysis sub-system determines that the images (or portions thereof) captured thus far do not provide sufficient evidence to generate screening/monitoring/diagnosis outcomes, the image capture process may be repeated to photograph additional regions of the eye as determined based on the disease(s) being screened/monitored/diagnosed. In certain embodiments of the system, the retinal geography check is performed by identifying anatomical structures of interest (including but not limited to, the macula, optic nerve head, vessels) using techniques described in [SBAB15].

Centering the Eye

Figure 8:
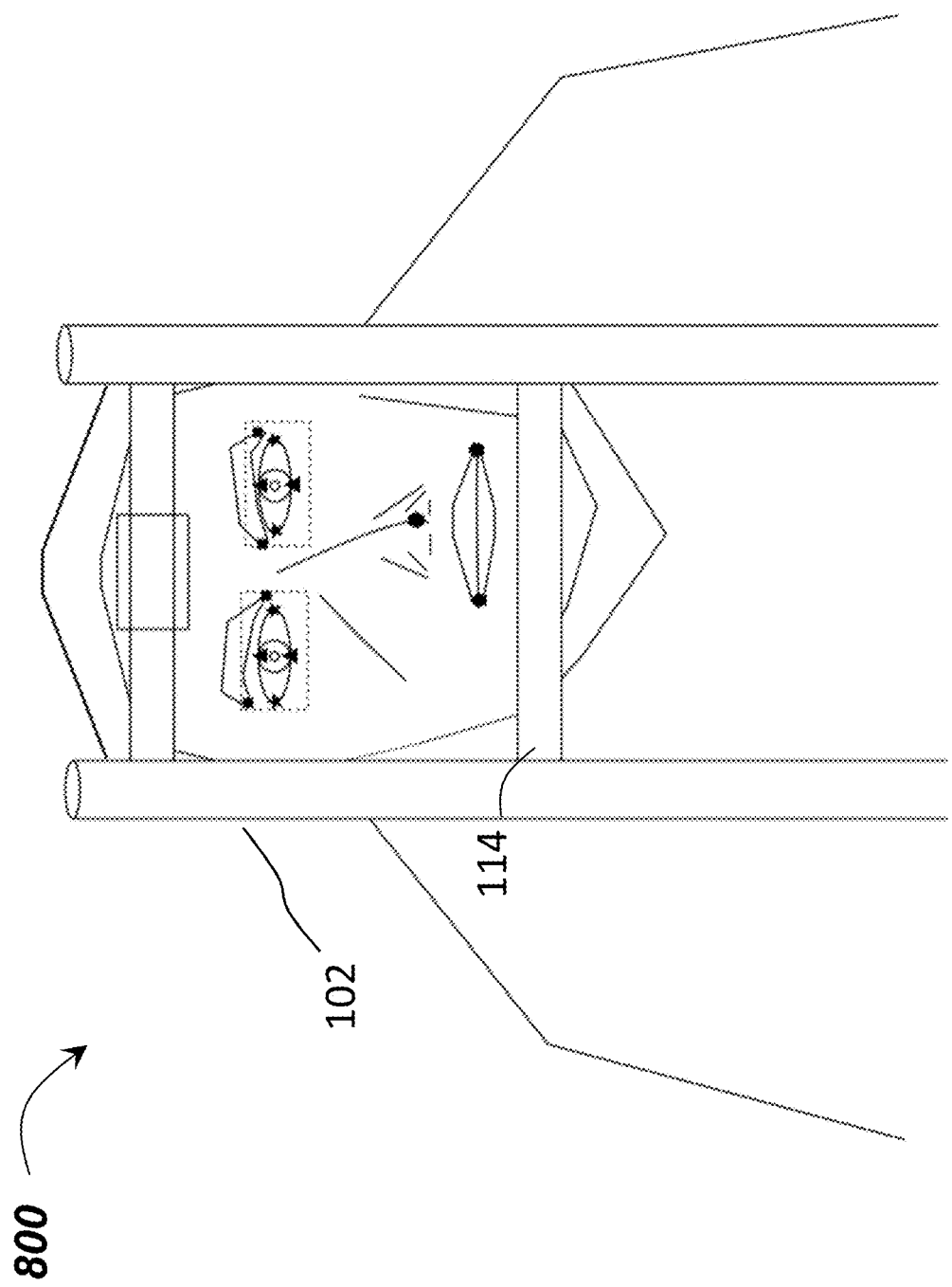
FIG. 8 illustrates exemplary facial landmarking of a patient on a head rest, in accordance with an embodiment of the present disclosure.

The task of centering the imaging device on the desired eye can be solved by making use of proven image-based face detection and facial landmark detection techniques as described in: "Dlib-ml: A Machine Learning Toolkit," King, Davis E., in: *Journal of Machine Learning Research* Bd. 10 (2009), Nr. Jul, S. 1755-1758 [King09]; "Deformable Model Fitting by Regularized Landmark Mean-Shift," Saragih, Jason M.; Lucey, Simon; Cohn, Jeffrey F., in: *International Journal of Computer Vision* Bd. 91 (2011), Nr. 2, S. 200-215 [SaLC11]; "Deep Convolutional Network Cascade for Facial Point Detection," Sun, Yi; Wang, Xiaogang; Tang, Xiaoou, in: *Proceedings of the* 2013 *IEEE Conference on Computer Vision and Pattern Recognition, CVPR '13.* Washington, D.C., USA: IEEE Computer Society, 2013—ISBN 978-0-7695-4989-7, S. 3476-3483 [SuWT13]; "Learning Deep Representation for Face Alignment with Auxiliary Attributes," Zhang, Zhanpeng; Luo, Ping; Loy, Chen Change; Tang, Xiaoou, in: *IEEE Transactions on Pattern Analysis and Machine Intelligence* Bd. 38 (2016), Nr. 5, S. 918-930.—arXiv: 1408.3967 [ZLLT16]; and "Coarse-to-Fine Auto-Encoder Networks (CFAN) for Real-Time Face Alignment," Zhang, Jie; Shan, Shiguang; Kan, Meina; Chen, Xilin, in: *Computer Vision—ECCV* 2014, *Lecture Notes in Computer Science*: Springer, Cham, 2014—ISBN 978-3-319-10604-5, S. 1-16 [ZSKC14]. Referring to FIG. 8, an example of face landmarking is illustrated. In certain embodiments of the system, the facial detection problem in this system may be constrained in multiple ways: the patient is in front of the imaging device; the patient is in a known frontal pose with a neutral facial expression; there is minimal occlusion of the face; (the head rest may occlude edges of the face). The search region for the system may be further constrained by the head rest 102 as shown in FIG. 8. Additionally, the system can reliably make use of three major facial landmarks: corner of the eyes, pupils, and eyebrows, due to the assumption that only one face, which could be partially occluded, will be present in the images captured at any point during the procedure. These constraints constitute a novel problem not addressed by existing image-based face detection and facial landmark detection techniques.

There exist many proven image-based face detection and facial landmark detection techniques. Some approaches use keypoint-based generic descriptors (e.g. SIFT, HoG, SURF) ("Supervised Descent Method and Its Applications to Face Alignment," Xiong, Xuehan; De la Torre, Fernando, in: *Proceedings of the* 2013 *IEEE Conference on Computer Vision and Pattern Recognition, CVPR* '13. Washington, D.C., USA: IEEE Computer Society, 2013—ISBN 978-0-7695-4989-7, S. 532-539 [XiDe13]; and "Face Alignment by Coarse-To-Fine Shape Searching," Zhu, Shizhan; Li, Cheng; Loy, C. C.; Tang, X., in: 2015 *IEEE Conference on Computer Vision and Pattern Recognition (CVPR)*, 2015, S. 4998-5006 [ZLLT15]) to detect facial features in systems trained for automated face alignment. More recent approaches have employed deep-learning based features [See, SuWT13, ZLLT16]. Although these features can be used to fit a template into the face ("Face Detection, Pose Estimation, and Landmark Localization in the Wild," Zhu, X.; Ramanan, D., in: 2012 *IEEE Conference on Computer Vision and Pattern Recognition,* 2012, S. 2879-2886 [ZhRa12]), a number of approaches [XiDe13, ZLLT15] apply cascaded regression techniques, where landmark locations are iteratively refined, some using deep learning methods ("Deep Recurrent Regression for Facial Landmark Detection," Lai, Hanjiang; Xiao, Shengtao; Pan, Yan; Cui, Zhen; Feng, Jiashi; Xu, Chunyan; Yin, Jian; Yan, Shuicheng (2015) [LXPC15]). Moreover, few systems ("Automatic Landmark Detection and 3D Face Data Extraction," Boukamcha, Hamdi; Hallek, Mohamed; Smach, Fethi; Atri, Mohamed, in: *Journal of Computational Science* Bd. 21 (2017), S. 340-348) [BHSA17]; and "3D Facial Landmark Detection under Large Yaw and Expression Variations," Perakis, P.; Passalis, G.; Theoharis, T.; Kakadiaris, I. A., in: *IEEE Transactions on Pattern Analysis and Machine Intelligence* Bd. 35 (2013), Nr. 7, S. 1552-1564 [PPTK13]) use 3D depth images to provide additional robustness in face landmarking.

In an embodiment, the system may use a multi-level approach to detect the landmarks around the eye. The initial estimation is done using landmark-detection algorithms such as provided in [King09] along with a deep-learning based solution trained using facial images, cropped to just show eyes. The finer estimation is done using a sliding-window approach with the aforementioned algorithms around the initial estimate of the eye location. After arriving at the final estimate, the imaging device is moved in 3-D space using the estimated location as a target, to center the eye in its field of view. This procedure is performed before approaching the working distance (as discussed in the MOVING TO WORKING DISTANCE section). In some embodiments, the system may utilize additional sensors to assist in determining the distance of the imaging device from the eye and thus the right working distance.

Moving to Working Distance

Figure 9:
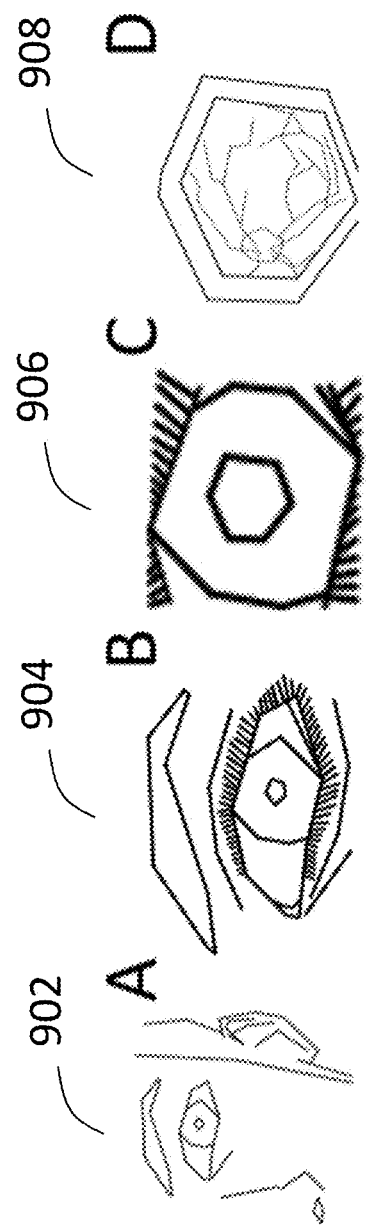
FIG. 9 illustrates four exemplary views of the imaging device as it fixes on the target eye and progressively moves towards the correct working distance to capture gradable images, in accordance with an embodiment of the present disclosure.

The images captured as the imaging device moves towards the eye (to get to the correct working distance) can be categorized into potentially multiple stages as illustrated in FIG. 9. In some embodiments, at each of the multiple stages the imaging device captures a progressively closer visible field of view of the eye.

At the beginning, the imaging device is sufficiently distant from the face to view the face 902 in sharp focus. As the imaging device moves towards the patient's target eye, a very limited region around the eye is visible in the field of view 904 and the eye is in focus. Further closer to the eye, a large portion of the field of view 906 is covered by the iris of the eye with the pupil being centered. In certain embodiments where the imaging device is a fundus camera, when the camera moves further in, portions of the retina become visible in the field of view 908 and at the correct working distance, the retinal plane is in focus and retinal vessels are visible and in focus.

Throughout the process of moving towards the working distance, it is important that the pupil stays centered in the image even with the occurrence of sudden eye movements or blinks. In some embodiments, the system may use cooperative landmark tracking and recognition of the eye.

Proven algorithms exist for visual tracking algorithms, like Mean-Shift tracking, as described in "Kernel-based Object Tracking," Comaniciu, D.; Ramesh, V; Meer, P., in: *IEEE Transactions on Pattern Analysis and Machine Intelligence* Bd. 25 (2003), Nr. 5, S. 564-577 [CoRM03] or KLT, as described in "Good features to track," Shi, Jianbo; Tomasi, C., in: 1994 *Proceedings of IEEE Conference on Computer Vision and Pattern Recognition,* 1994, S. 593-600 [ShTo94]. However, these algorithms are developed for problems where the moving object is at near-constant depth from the viewer, which is not always the case, where embodiments of the present disclosure can operate in. One approach to tracking involves creating templates of the target object/region (pupil, eye, and immediate facial surroundings) at various depths and recording the smooth changes expected between images captured at different time instances. These templates can utilize many features including but not limited to textures and key-points and its configurations (see "Object Tracking Using SIFT Features and Mean Shift," Zhou, Huiyu; Yuan, Yuan; Shi, Chunmei, in: *Computer Vision and Image Understanding, Special Issue on Video Analysis*. Bd. 113 (2009), Nr. 3, S. 345-352 [ZhYS09]), histogram of an area ([CoRM03]), or a combination of these.

"Tracking-Learning-Detection," Kalal, Z.; Mikolajczyk, K.; Matas, J., in: *IEEE Transactions on Pattern Analysis and Machine Intelligence* Bd. 34 (2012), Nr. 7, S. 1409-1422 [KaMM12] looks at the problem a step further in their Tracking-Learning-Detection (TLD) tracker that not only detects, tracks, and updates the target's appearance, but also understands the distractors in the environment.

In recent years, deep neural network target trackers (as described in "Deep Track: Learning Discriminative Feature Representations Online for Robust Visual Tracking," Li, Hanxi; Li, Yi; Porikli, Fatih, in: *IEEE Transactions on Image Processing* Bd. 25 (2016), Nr. 4, S. 1834-1848.—arXiv: 1503.00072 [LiLP16]; "Learning Multi-Domain Convolutional Neural Networks for Visual Tracking," Nam, Hyeonseob; Han, Bohyung, in: *arXiv:* 1510.07945 [*cs*] (2015).—arXiv: 1510.07945 [NaHa15]; "Learning a Deep Compact Image Representation for Visual Tracking," Wang, Naiyan; Yeung, Dit-Yan, in: Burges, C. J. C.; Bottou, L.; Welling, M.; Ghahramani, Z.; Weinberger, K. Q. (Hrsg.): *Advances in Neural Information Processing Systems* 26: Curran Associates, Inc., 2013, S. 809-817 [WaYe13]; and "Robust Visual Tracking via Convolutional Networks," Zhang, Kaihua; Liu, Qingshan; Wu, Yi; Yang, Ming-Hsuan, in: *arXiv:* 1501.04505 [*cs*] (2015).—arXiv: 1501.04505 [ZLWY15]) have become the state-of-the-art as they improved performances with respect to more extreme object rotation, view-point, and lighting. Their common characteristic is that they require online training to allow tracking of objects not included during offline training, which can be slow. However, in an embodiment of the present disclosure, due to the constrained nature of the tracking problem, the training may be done off-line or significantly earlier than testing.

In addition to tracking the pupil while the imaging device is moving towards the eye, the system also needs to determine when to stop. The system can tolerate a small error margin from the optimal working distance if it captures multiple images when close to the optimal working distance. In some embodiments, the image acquisition process may have to reset if a sufficient number of gradable images is not available. Therefore, in some embodiments, the entire problem of arriving at the optimal working distance can be reformulated with machine learning, for example as a reinforcement learning (RL) task. Given sensor inputs, a machine learning module, for example an RL module, can directly output motor commands to the moving platform that will move the imaging device exactly to the working distance. Here reinforcement learning simultaneously solves the pupil tracking/detection problem as well as the determination of the optimal working distance. In an additional embodiment, deep reinforcement learning (deep-RL), popularized by "Human-Level Control Through Deep Reinforcement Learning," Mnih, Volodymyr; Kavukcuoglu, Koray; Silver, David; Rusu, Andrei A.; Veness, Joel; Bellemare, Marc G.; Graves, Alex; Riedmiller, Martin; u. a., in: *Nature* Bd. 518 (2015), Nr. 7540, S. 529-533 [MKSR15], allows for end-to-end learning by making use of the representational learning of deep learning and objective learning of reinforcement learning.

In some embodiments, the system of the present disclosure employs a combination of multiple tracking techniques. The system may use the TLD tracker [KaMM12], using their standard features, but also incorporating the face landmarking algorithms of [King09]. In addition, system may supplement the tracker with proximity sensors. The system may also include a deep-RL system that can make use of other sensory inputs (in addition to the images), such as encoder values from the motors. This way the technique can correlate physical measurements and distances to ground the system and limit the search area.

Image Quality Assessment

The problem of Image Quality Assessment (IQA) is to deem an image as gradable by checking for a number of parameters. In certain embodiments where the image is a retinal fundus image, the parameters to be checked include but are not limited to, sufficient quality for visualization of anatomical structures and lesions, proper focusing of the image, and correct illumination of the image to allow for a clear and focused view of the retinal vessels.

One class of image quality assessment techniques use features including image characteristics information. These may include illumination and sharpness (as described in "Evaluation of Retinal Image Gradability by Image Features Classification," Dias, João Miguel Pires; Oliveira, Carlos Manta; Cruz, Luís A. da Silva, in: *Procedia Technology*, 4th *Conference of ENTERprise Information Systems—aligning technology, organizations and people (CENTERIS 2012)*. Bd. 5 (2012), S. 865-875 [DiOC12]); landmark structures like the retinal vessels and the optic nerve head within the image (as described in "Quality Assessment of Retinal Fundus Images Using Elliptical Local Vessel Density," Giancardo, Luca; Meriaudeau, Fabrice; Karnowski, Thomas P.; Chaum, Edward; Tobin, Kenneth, in: *New Developments in Biomedical Engineering, Ed. Domenico Campolo, INTECH. http://sciyo.com/books/show/title/new-developments-in-biomedical-engineering* (2010) [GMKC10]; and "Automatic Fundus Image Field Detection and Quality Assessment," Katuwal, G. J.; Kerekes, J.; Ramchandran, R.; Sisson, C.; Rao, N, in: *Image Processing Workshop (WNYIPW), 2013 IEEE Western New York*, 2013, S. 9-13 [KKRS13]); or a combination of characteristic measures and structure based information (as described in "Automated Quality Assessment of Retinal Fundus Photos," Paulus, Jan; Meier, Jörg; Bock, Rüdiger; Hornegger, Joachim; Michelson, Georg, in: *International journal of computer assisted radiology and surgery* Bd. 5 (2010), Nr. 6, S. 557-564 [PMBH10]; and in [SBAB15]).

Another class of techniques combine such localized features across the whole image ([DiOC12]). However, such a method would not allow for the detection of localized image quality issues and/or artifacts. Structure-based approaches can use raw pixels to create higher-level blobs, which can be then traced back to contours and ultimately structures within the image ([GMKC10]), thus creating a full structural picture of the image that is highly robust.

The newest class of techniques rely on deep learning methods (see, "Retinal Image Quality Classification Using Saliency Maps and CNNs," Mahapatra, Dwarikanath; Roy, Pallab K.; Sedai, Suman; Garnavi, Rahil, in: *Machine Learning in Medical Imaging, Lecture Notes in Computer Science*: Springer, Cham, 2016—ISBN 978-3-319-47156-3, S. 172-179 [MRSG16]; and "Deep Learning for Automated Quality Assessment of Color Fundus Images in Diabetic Retinopathy Screening," Saha, Sajib Kumar; Fernando, Basura; Cuadros, Jorge; Xiao, Di; Kanagasingam, Yogesan, in: *arXiv:* 1703.02511 [*cs*] (2017).—arXiv: 1703.02511 [SFCX17]) where neural networks are trained for image quality assessment on a labeled dataset with images of varying qualities. This approach eliminates the need for hand-crafting features and methods of combining them, while simultaneously encoding notions of blob-level grouping and connectedness.

In some embodiments, the system of the present disclosure is a deep learning based system trained using a labeled dataset of fundus images with varying quality, expanded by data augmentation. In some embodiments, a deep learning based system is used to determine the quality of portions of fundus images.

Retinal Coverage Assessment

This sub-system is used, in some embodiments, where the images captured are fundus/retinal images. To generate a screening/diagnosis report, the system needs images that visualize a wide region of the retina. Off-the-shelf imaging devices usually have a limited field of view and thus cannot capture all the regions required for generating the report in a single image. This presents the need for multiple images of the retina. The system captures one or more images of different regions of the retina. To ensure that all required regions are present in the images captured by the imaging device, the system will make use of proven algorithms to detect retinal fields (such as, but not limited to, optical nerve head-centered view, and macula-centered view) in an image that correspond to regions of the retina.

In some embodiments, the system of the present disclosure employs machine learning, for example deep-learning methods to detect the retinal field present in the image. The deep learning system is trained using a dataset of fundus images labeled with the retinal field they represent, and this dataset is expanded by data augmentation. In conjunction with the deep-learning methods used for image quality assessment, these systems will aggregate gradable images in a way that the selected images, collectively, represent a view of all retinal fields necessary for providing a screening/diagnosis report.

While embodiments of the present invention have been shown and described, various modifications may be made without departing from the spirit and scope of the present invention, and all such modifications and equivalents are intended to be covered.

As used herein and in the appended claims, the singular forms "a", "an", and "the" include plural referents unless the context clearly dictates otherwise.

In the following description and in the figures, like elements are identified with like reference numerals. The use of "e.g.," "etc.," and "or" indicates non-exclusive alternatives without limitation, unless otherwise noted. The use of "including" or "includes" means "including, but not limited to," or "includes, but not limited to," unless otherwise noted.

As used herein, the term "and/or" placed between a first entity and a second entity means one of (1) the first entity, (2) the second entity, and (3) the first entity and the second entity. Multiple entities listed with "and/or" should be construed in the same manner, i.e., "one or more" of the entities so conjoined. Other entities may optionally be present other than the entities specifically identified by the "and/or" clause, whether related or unrelated to those entities specifically identified. Thus, as a non-limiting example, a reference to "A and/or B", when used in conjunction with open-ended language such as "comprising" can refer, in one embodiment, to A only (optionally including entities other than B); in another embodiment, to B only (optionally including entities other than A); in yet another embodiment, to both A and B (optionally including other entities). These entities may refer to elements, actions, structures, steps, operations, values, and the like.

Various aspects will be presented in terms of systems that may include several components, modules, and the like. It is to be understood and appreciated that the various systems may include additional components, modules, etc. and/or may not include all the components, modules, etc. discussed in connection with the figures. A combination of these approaches may also be used. The various aspects disclosed herein can be performed on electrical devices including devices that utilize touch screen display technologies and/or mouse-and-keyboard type interfaces. Examples of such devices include computers (desktop and mobile), smart phones, personal digital assistants (PDAs), and other electronic devices both wired and wireless.

In addition, the various illustrative logical blocks, modules, and circuits described in connection with the aspects disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

Operational aspects disclosed herein may be embodied directly in hardware, in a software module executed by a processor, or in a combination of the two. A software module may reside in RAM memory, flash memory, ROM memory, EPROM memory, EEPROM memory, registers, hard disk, a removable disk, a CD-ROM, or any other form of storage medium known in the art. An exemplary storage medium is coupled to the processor such the processor can read information from, and write information to, the storage medium. In the alternative, the storage medium may be integral to the processor. The processor and the storage medium may reside in an ASIC. The ASIC may reside in a user terminal. In the alternative, the processor and the storage medium may reside as discrete components in a user terminal.

Furthermore, the one or more versions may be implemented as a method, apparatus, or article of manufacture using standard programming and/or engineering techniques to produce software, firmware, hardware, or any combination thereof to control a computer to implement the disclosed aspects. Non-transitory computer readable media can include but are not limited to magnetic storage devices (e.g., hard disk, floppy disk, magnetic strips . . . ), optical disks (e.g., compact disk (CD), digital versatile disk (DVD), BluRay™ . . . ), smart cards, solid-state devices (SSDs), and flash memory devices (e.g., card, stick). Of course, those skilled in the art will recognize many modifications may be made to this configuration without departing from the scope of the disclosed aspects.

The publications discussed herein are provided solely for their disclosure prior to the filing date of the present application. Nothing herein is to be construed as an admission that the present disclosure is not entitled to antedate such publication by virtue of prior disclosure. Further, the dates of publication provided may be different from the actual publication dates which may need to be independently confirmed.

It should be noted that all features, elements, components, functions, and steps described with respect to any embodiment provided herein are intended to be freely combinable and substitutable with those from any other embodiment. If a certain feature, element, component, function, or step is described with respect to only one embodiment, then it should be understood that that feature, element, component, function, or step can be used with every other embodiment described herein unless explicitly stated otherwise. This paragraph therefore serves as antecedent basis and written support for the introduction of claims, at any time, that combine features, elements, components, functions, and steps from different embodiments, or that substitute features, elements, components, functions, and steps from one embodiment with those of another, even if the following description does not explicitly state, in a particular instance, that such combinations or substitutions are possible. It is explicitly acknowledged that express recitation of every possible combination and substitution is overly burdensome, especially given that the permissibility of each and every such combination and substitution will be readily recognized by those of ordinary skill in the art. In many instances, entities are described herein as being coupled to other entities. It should be understood that the terms "coupled" and "connected" (or any of their forms) are used interchangeably herein and, in both cases, are generic to the direct coupling of two entities (without any non-negligible (e.g., parasitic) intervening entities) and the indirect coupling of two entities (with one or more non-negligible intervening entities). Where entities are shown as being directly coupled together or described as coupled together without description of any intervening entity, it should be understood that those entities can be indirectly coupled together as well unless the context clearly dictates otherwise.

While the embodiments are susceptible to various modifications and alternative forms, specific examples thereof have been shown in the drawings and are herein described in detail. It should be understood, however, that these embodiments are not to be limited to the particular form disclosed, but to the contrary, these embodiments are to cover all modifications, equivalents, and alternatives falling within the spirit of the disclosure. Furthermore, any features, functions, steps, or elements of the embodiments may be recited in or added to the claims, as well as negative limitations that define the inventive scope of the claims by features, functions, steps, or elements that are not within that scope.

What is claimed is:

1. An automated system for end-to-end eye screening, monitoring, and diagnosing of one or more diseases or disorders comprising:
a moving platform;
a head rest coupled to the moving platform;
a computing platform coupled to the moving platform, wherein the computing platform comprises a user interface sub-system, an image acquisition sub-system, an image analysis sub-system, and a screening and diagnosis report sub-system;
an imaging device coupled to the moving platform and configured for capturing one or more images of an eye of a patient;
a controller coupled to the moving platform and to the computing platform, wherein the controller is configured for controlling the movement of the imaging device in three-dimensional space;
a machine learning module, wherein the machine learning module receives and uses sensor inputs from one or more sensors to output commands to the moving platform to move the imaging device to a working distance from the eye of the patient; and
wherein the image analysis sub-system is configured for analyzing the captured one or more images to provide one or more results of the screening, monitoring, and diagnosing.

2. The automated system of claim 1 further comprises an electronic display device or a printer for displaying or printing the one or more results of the screening, monitoring, and diagnosing.

3. The automated system of claim 1 wherein the one or more sensors comprise one or more guidance and safety sensors and mechanisms.

4. The automated system of claim 3, wherein the one or more guidance and safety sensors comprise at least one of proximity sensor and proprioceptive sensor.

5. The automated system of claim 1, wherein the controller controls the movement of the imaging device towards a working distance from the eye of the patient in multiple stages.

6. The automated system of claim 5, wherein at each of the multiple stages the imaging device captures a progressively closer visible field of view of the eye of the patient.

7. The automated system of claim 1, wherein movement of the imaging device is automatically controlled by the image acquisition sub-system via the controller.

8. The automated system of claim 1, wherein movement of the imaging device is assisted by an operator.

9. The automated system of claim 8, wherein the operator uses a joystick or a touch-activated electronic display, or voice commands to assist the movement of the imaging device.

10. The automated system of claim 9, wherein the automated system is activated using one of a button/switch, the touch-activated electronic display, pressure-sensors in the head rest, and a voice-activated command.

11. The automated system of claim 1, wherein the controller is coupled to a plurality of sets of motors, each set is configured for controlling motion of the imaging device along one of a spatial x-axis, a spatial y-axis, and a spatial z-axis.

12. The automated system of claim 1, wherein the controller controls the movement of the imaging device in desired safety limits.

13. The automated system of claim 1, wherein the controller controls the movement of the imaging device in accordance to current dynamics.

14. The automated system of claim 1, wherein the imaging device captures multiple images of a retina of the eye of the patient, where each image captures a different region of the retina.

15. The automated system of claim 1, wherein the image analysis sub-system analyzes the captured one or more images based on one or more of visualization of anatomical structures and lesions, proper focusing of the image, and correct illumination of the image to allow for a clear and focused view of the retinal vessels.

16. The automated system of claim 1, wherein the automated system employs one or more deep-learning methods to detect a retinal field present in the one or more captured images of the eye of the patient.

17. The automated system of claim 16, wherein the one or more deep-learning methods is a neural network.

18. An automated system for end-to-end eye screening, monitoring, and diagnosing of one or more diseases or disorders comprising:
a moving platform;
a head rest coupled to the moving platform;
a computing platform coupled to the moving platform, wherein the computing platform comprises a user interface sub-system, an image acquisition sub-system, an image analysis sub-system, and a screening and diagnosis report sub-system;
an imaging device coupled to the moving platform and configured for capturing one or more images of an eye of a patient;
a controller coupled to the moving platform and to the computing platform, wherein the controller is configured for controlling the movement of the imaging device in three-dimensional space;
wherein the automated system tracks a pupil of the eye of the patient while the imaging device is moving towards the eye of the patient; and
wherein the image analysis sub-system is configured for analyzing the captured one or more images to provide one or more results of the screening, monitoring, and diagnosing.

19. The automated system of claim 18, wherein the automated system employs a combination of multiple tracking techniques.

* * * * *